(12) United States Patent
Nedwed et al.

(10) Patent No.: US 9,834,460 B2
(45) Date of Patent: Dec. 5, 2017

(54) METHOD AND SYSTEM FOR USING SUBSEA DISPERSANTS

(71) Applicants: Timothy J. Nedwed, Houston, TX (US); David A. Palandro, The Woodlands, TX (US); Amy C. Tidwell, Houston, TX (US)

(72) Inventors: Timothy J. Nedwed, Houston, TX (US); David A. Palandro, The Woodlands, TX (US); Amy C. Tidwell, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 432 days.

(21) Appl. No.: 14/550,451

(22) Filed: Nov. 21, 2014

(65) Prior Publication Data

US 2015/0175452 A1 Jun. 25, 2015

Related U.S. Application Data

(60) Provisional application No. 61/918,354, filed on Dec. 19, 2013.

(51) Int. Cl.
*C02F 1/68* (2006.01)
*E02B 15/04* (2006.01)
(Continued)

(52) U.S. Cl.
CPC ............ *C02F 1/682* (2013.01); *E02B 15/041* (2013.01); *E21B 43/0122* (2013.01);
(Continued)

(58) Field of Classification Search
CPC .... C02F 1/008; C02F 1/40; C02F 1/68; C02F 1/681; C02F 1/682; C02F 1/685;
(Continued)

(56) References Cited

U.S. PATENT DOCUMENTS

| | | | |
|---|---|---|---|
| 5,176,831 A | * | 1/1993 | Rowsell .................... B09C 1/00 210/631 |
| 5,490,940 A | | 2/1996 | Bragg et al. |

(Continued)

FOREIGN PATENT DOCUMENTS

WO WO2011/156867 12/2011

OTHER PUBLICATIONS

Richard Camilli et al, "Tracking Hydrocarbon Plume Transport and Degradation at Deepwater Horizon", Science, vol. 330, Oct. 8, 2010, pp. 201-204.*

(Continued)

*Primary Examiner* — Joseph Drodge
(74) *Attorney, Agent, or Firm* — ExxonMobil Upstream Research Company—Law Department

(57) ABSTRACT

Method and system is described to enhance operations for managing the hydrocarbon release. The method and system for managing a hydrocarbon release includes one or more vessels configured to collect mineral fines, to transfer the mineral fines to a hydrocarbon, and inject the mineral fines into the hydrocarbons at or near the hydrocarbon release location. The method may include subsea dredging or sediment collection in the vicinity of the mineral fines injection. This approach may be utilized to provide a continuous supply of material without interruption to injection operations.

22 Claims, 3 Drawing Sheets

(51) Int. Cl.
*G01N 33/18* (2006.01)
*E21B 43/01* (2006.01)
*C02F 101/32* (2006.01)
*C02F 103/00* (2006.01)
*C02F 103/08* (2006.01)

(52) U.S. Cl.
CPC ...... *G01N 33/1826* (2013.01); *C02F 2101/32* (2013.01); *C02F 2103/007* (2013.01); *C02F 2103/08* (2013.01); *C02F 2209/00* (2013.01)

(58) Field of Classification Search
CPC ................ C02F 1/687; C02F 2101/32; C02F 2101/325; C02F 2103/007; C02F 2103/08; C02F 2209/00; C02F 2209/11; B01D 17/00; B01D 17/04; B01D 17/048; B01D 17/12; E02B 5/00; E02B 5/04; E02B 5/041; E02B 15/00; E02B 15/04; E02B 15/041; E02B 15/045; E02B 15/046; E21B 43/01; E21B 43/0122; E02F 1/00; E02F 3/00; E02F 5/00; E02F 5/006; E02F 9/20; E02F 9/2004; E02F 9/2025; E02F 9/205; G01N 1/10; G01N 1/12; G01N 21/00; G01N 21/01; G01N 21/25; G01N 33/18; G01N 33/1826; G01N 33/1833; G01N 2001/1031; G01N 2121/0181; G01N 2121/8405; G01N 2121/0162; G01N 2121/0187; G01N 2021/0162; G01N 2021/0181; G01N 2021/0187
USPC ................ 37/307, 308, 309, 313, 314, 345; 73/53.01, 61.41, 61.43, 61.44, 61.48, 73/61.62, 61.71, 64.56, 170.29, 170.32, 73/863, 863.01, 864, 864.31; 210/85, 94, 210/96.1, 170.01, 170.11, 696, 739, 745, 210/747.1, 747.4, 747.5, 923, 924, 925, 210/708, 747.6; 356/36, 402, 425, 432, 356/433; 702/50

See application file for complete search history.

(56) References Cited

U.S. PATENT DOCUMENTS

| | | | | |
|---|---|---|---|---|
| 6,374,519 | B1* | 4/2002 | Beaumont | E02F 3/88 37/307 |
| 7,150,996 | B2* | 12/2006 | Nicoli | G01N 15/1456 422/68.1 |
| 2008/0068926 | A1* | 3/2008 | Chambers | G01S 15/96 367/7 |
| 2011/0315233 | A1* | 12/2011 | Carter | E21B 43/0122 137/14 |
| 2012/0186822 | A1* | 7/2012 | Mahajan | E21B 43/0122 166/364 |
| 2012/0201604 | A1* | 8/2012 | Drieu | E21B 43/0122 405/62 |
| 2012/0217195 | A1* | 8/2012 | Morgenthaler | E21B 43/0122 210/170.05 |
| 2013/0063300 | A1* | 3/2013 | O'Regan | E02B 15/00 342/357.25 |
| 2013/0075337 | A1* | 3/2013 | Lochhead | B01F 17/0028 210/699 |

OTHER PUBLICATIONS

Helen Chapman et al, "The use of chemical dispersants to combat oil spills at sea: A review of practive and research needs in Europe", Marine Pollution Bulletin vol. 54, pp. 827-838, 2007.*
Mark Reed et al, "Oil Spill Modeling towards the Close of the 20th Century: Overview of the State of the Art", Spill Science & Technology Bulletin, vol. 5, No. 1, pp. 3-16, 1999.*
Mark Reed et al, "Modelling of dispersant application to oil spills in shallow coastal waters", Environmental Modeling & Software, vol. 19, pp. 681-690, 2004.*
John Allen et al, "Enhanced Oil Spill Surveillance, Detection and Monitoring through the Applied Technology of Unmanned Air Systems", International Oil Spill Conference Proceedings, vol. 2008, Issue 1, May 2008, cover page and Abstract.*
John Allen et al, "Enhanced Oil Spill Surveillance, Detection and Monitoring through the Applied Technology of Unmanned Air Systems", International Oil Spill Conference Proceedings, vol. 2008, Issue 1, May 2008, full text, pp. 113-120.*
Lee, K.Z. et al. (2009), "In-situ Remediation of Oil Spills in Ice-Infested Waters: Oil Dispersion by Enhancing Formation of Oil-Mineral Aggregates," In Proceedings of the 2009 Interspill Conference, Marseille, France, 17 pages.
API (2013) "*Industry Recommended Subsea Dispersant Monitoring Plan*" Technical Report 1152; Sep. 2013.
ExxonMobil, (2013) "*Offshore Arctic Oil Spill Prevention, Preparedness and Response*" http://cdn.exxonmobil.com/~/media/global/files/energy-and-environment/news_pub_2013-arctic-spill-prevent.pdf, retrieved Jul. 15, 2015 by WIPO.
Ridley, et al. (2011) "*Seafloor Production Tools for the Resources of the Future*" OTC 21443; May 2-5, 2011.

* cited by examiner

METHOD AND SYSTEM FOR USING SUBSEA DISPERSANTS

CROSS-REFERENCE TO RELATED APPLICATION

This application claims the benefit of U.S. Provisional Patent Application 61/918,354, filed Dec. 19, 2013, entitled METHOD AND SYSTEM FOR USING SUBSEA DISPERSANTS, the entirety of which is incorporated by reference herein.

FIELD OF THE INVENTION

This invention relates generally to the field of hydrocarbon operations. Specifically, the invention relates to operations for managing oil releases, which utilizes mineral fines for subsea dispersant injection.

BACKGROUND

This disclosure relates generally to the field of hydrocarbon operations. In particular, the disclosure relates to operations for managing oil releases, which utilize mineral fines for subsea dispersant injection.

This section is intended to introduce various aspects of the art, which may be associated with one or more embodiments of the present disclosure. This discussion is believed to assist in providing a framework to facilitate a better understanding of particular aspects of the present disclosure. Accordingly, it should be understood that this section should be read in this light, and not necessarily as admissions of prior art.

In the oil and gas industry, hydrocarbons are accessed via a wellbore to provide a fluid flow path to a processing facility. Some of these hydrocarbon resources are located under bodies of water, such as lakes, seas, bays, rivers and/or oceans, while others are located at onshore locations. To transfer hydrocarbons from such locations, a pipeline and/or one or more different vessels (e.g., ship or tanker trucks) may be utilized through various segments from the wellbore and the processing facility.

Offshore leaks and/or spills may be problematic due to the hydrocarbons being released into a body of water. Typically, the hydrocarbons may form a slick on the surface of the water, which may be referred to as an oil slick. These oil slicks may form from hydrocarbons being released from subsea equipment or associated tubular members providing flow paths for hydrocarbons from subsurface formations.

Accordingly, various response techniques may be utilized to manage the hydrocarbon release and any associated oil slicks. One technique to manage the hydrocarbons released within a body of water is chemical dispersants. As an example, subsea chemical dispersant injection may be utilized for a subsea well blowout to reduce the amount of oil reaching the surface and ultimately stranding on shorelines. The use of subsea chemical dispersants may involve forming and maintaining stockpiles of chemical dispersant located near a well site (e.g., usually in vessels on the surface of the body of water), a pump and a conduit to transfer the chemical dispersant to a discharge point near any hydrocarbon release location, and a nozzle system or other system to inject the dispersant into the flowing hydrocarbons. If a well-control event occurs and hydrocarbons are escaping to the sea near the seabed, injecting chemical dispersants using this system into the flowing hydrocarbons escaping from the well causes the hydrocarbons to break up into very small oil droplets. These oil droplets have very slow rise velocities and may potentially stay in the water column indefinitely until most of the oil in the individual droplets is biodegraded by petroleum degrading bacteria.

Industry has developed contingency plans to use subsea chemical dispersant injection for drilling operations. These plans require establishing large chemical dispersant stockpiles of commercially available dispersants to meet requirements for worst case discharge flows. Further, although these chemical dispersant stockpiles are large, a worst-case discharge flow rate may exhaust the chemical dispersant stockpile in days to weeks. Once exhausted, any chemical dispersant resupply may involve re-allocating from other chemical dispersant stockpiles or by manufacturing additional chemical dispersants. Although industry has developed robust systems to ensure continued supply of dispersants during an emergency, stockpile transfer and manufacture are logistical challenges.

Suspended particulate matter (SPM) may be utilized to remobilize and disperse stranded hydrocarbons. As an example, U.S. Pat. No. 5,490,940 describes adding to the surface a mixture of fine hydrophilic mineral solids dispersed in an aqueous liquid that interacts with the oil to form buoyant mineral fines-oil floccules. These floccules reduce the tendency of the oil to adhere to solid surfaces or to re-coalesce, thus facilitating dispersion and removal of the oil.

The suspended particulate matter (SPM) techniques have also been utilized and further developed by the Department of Fisheries and Oceans (DFO) Canada. The DFO Canada and the Canadian Coast Guard conducted a field test in the St. Lawrence River to study the use of mineral fines to disperse oil slicks in concentrated ice. See, e.g., Lee, K., Z. Li, B. Robinson, P. E. Kepkay, X. Ma, S. Cobanli, T. King, M. Blouin, and B. Doyon. 2009. In-situ Remediation of Oil Spills in Ice-Infested Waters: Oil Dispersion by Enhancing Formation of Oil-Mineral Aggregates. In Proceedings of the 2009 Interspill Conference, 12-14 May 2009, Marseille, France. During this test, calcite-based fines were sprayed on surface oil slicks in ice and then the oil slicks were subjected to the prop wash of an icebreaker used to conduct the test. The icebreaker prop wash rapidly converted the surface oil slicks into oil plumes that transferred into the water column. The mineral treated oil formed stable dispersions and showed no evidence of resurfacing, while the untreated oil (i.e. subjected to same mixing but with no mineral fines applied) did not disperse effectively.

As the management of hydrocarbon leaks and oil spills is a time consuming operation, a need exists to enhance operations to manage hydrocarbon releases with enhanced methods and systems. In particular, a need exists for a new technique that is an alternative or supplement to the use of chemical dispersants in subsea dispersant injection. Injection of mineral fines is an alternative technique that may be utilized.

SUMMARY

This summary is meant to provide an introduction of the various embodiments further described herein and is not meant to limit the scope of claimed subject matter.

In one aspect, a method for managing a hydrocarbon release with a hydrocarbon release management system is described. The method comprising: obtaining mineral fines; injecting the mineral fines into the hydrocarbon release; measuring characteristics of a hydrocarbon plume resulting from the hydrocarbon release; and determining whether to adjust the injection operations based on the measurements.

In another aspect, a hydrocarbon release management system is described. The system may include injection equipment configured to inject mineral fines into a hydrocarbon release.

Other aspects of the present disclosure will be apparent from the following description and the appended claims.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

Figure 1:
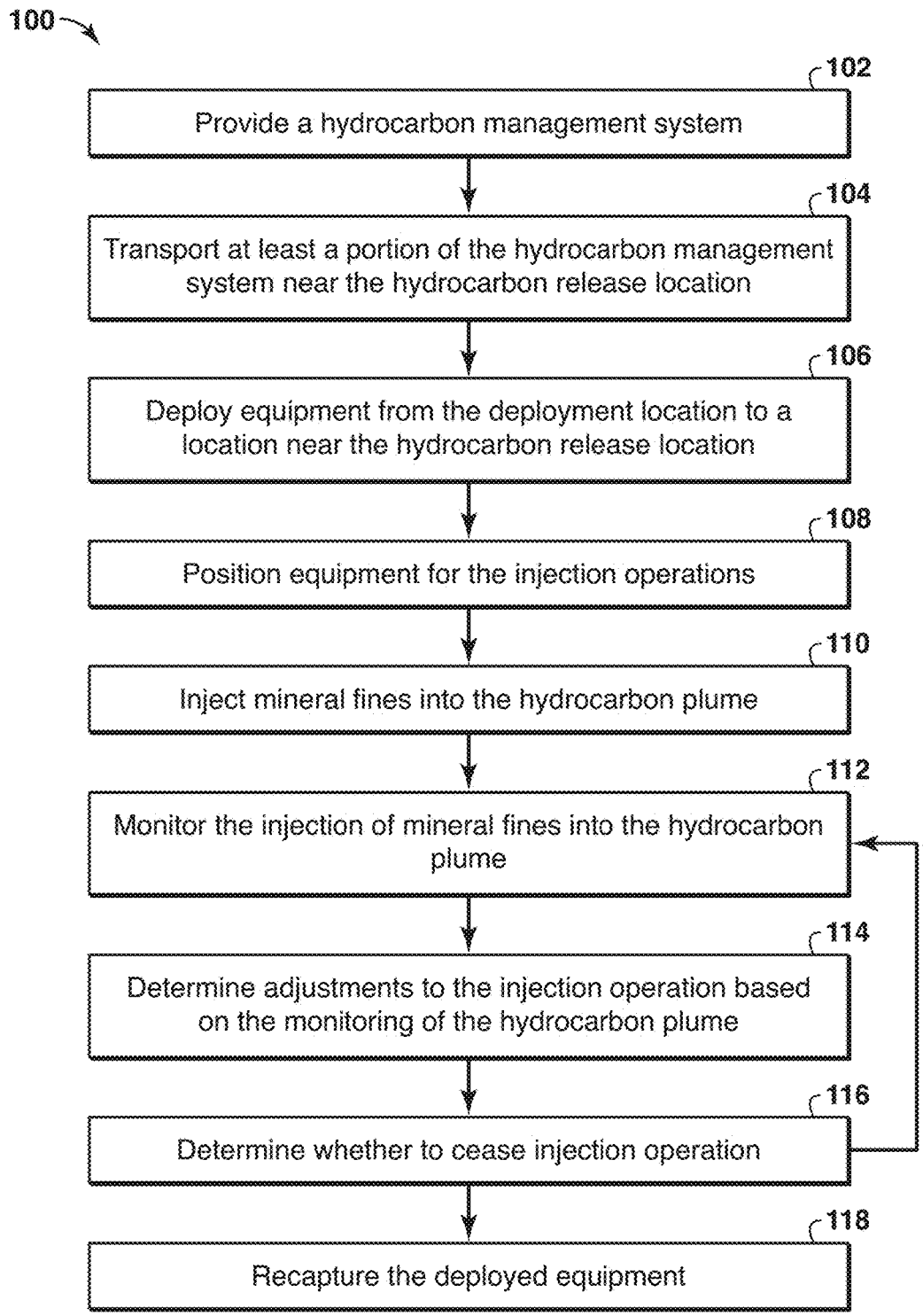
FIG. 1 is flow chart for performing oil release management in accordance with one or more embodiments of the present disclosure.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

The term, "mineral" as used herein means an element or chemical compound that is normally crystalline and has been formed as a result of geological processes.

The term, "fines", as used herein means silts and clays. For example, coarse silts may include particles from 31 micrometers to 63 micrometers, medium silt may include particles from 15.6 micrometers to 31 micrometers, fine silt may include particles from 7.8 micrometers to 15.6 micrometers, very fine silt may include particles from 3.9 micrometers to 7.8 micrometers, and clays may include particles from 0.06 micrometers to less than 3.9 micrometers. Mineral fines may be obtained from one or more locations remote from the hydrocarbon release and/or near the hydrocarbon release. Sources of mineral fines may include mining operations and/or dredging operations from bodies of water.

The term "sand" is meant to include mineral fines having a particle size in the range of from greater than 63 microns to at most 2000 micrometers.

The term "silt" is meant to include mineral fines having a particle size in the range of from 3.9 microns to 63 microns.

The term "clay minerals" is meant to include mineral fines having a particle size of less than 3.9 microns.

The present disclosure describes a method and system to replace or supplement the use of chemical dispersants in subsea dispersant injection with the injection of mineral fines. The particle size of the mineral fine particles may be controlled to enhance the ability of the mineral fines to disperse hydrocarbons in the hydrocarbon release management operations. In one or more embodiments, the mineral fines may have a particle size of at less than or equal to 63 micrometers (also referred herein as "microns") which correlates to particles passing through a 0.063 mm sieve. In one or more embodiments, the mineral fines may be a silt having a particle size less than or equal to 31 microns which correlates to particles passing through a 0.031 mm sieve, silt having a particle size less than or equal to 15.6 microns which correlates to particles passing through a 0.0156 mm sieve, or silt having a particle size less than or equal to 7.8 microns, which correlates to particles passing through a 0.0078 mm sieve. The above mineral fines may be limited in size by retaining particles below a certain size through the use of a 0.0039 mm sieve, a 0.0078 mm sieve, a 0.0156 mm sieve and/or a 0.031 mm sieve. Accordingly, in one or more embodiments, the mineral fines may include silt having a particle size in the range of 3.9 microns to 63 microns which correlates to particles passing through a 0.063 mm sieve and retained by a 0.0039 mm sieve, or silt having a particle size in the range of 3.9 microns to 31 microns which correlates to particles passing through a 0.031 mm sieve and retained by a 0.0039 mm sieve, silt having a particle size in the range of 3.9 microns to 15.6 microns which correlates to particles passing through a 0.0156 mm sieve and retained by a 0.0039 mm sieve, or silt having a particle size in the range of 3.9 mm to 7.8 microns which correlates to particles passing through a 0.0078 mm sieve and retained by a 0.0039 mm sieve. In one or more embodiments, the mineral fines may comprise clay minerals having a particle size of less than 3.9 microns. For the particle sizes described, it is intended that the majority of mineral fines may fall within the particle size value described in a particular embodiment, for example at least 80 percent (%) or at least 90% of the mineral fines may fall within the particle size value described in a particular embodiment.

Particle size measurements for particles having a particle size of at least 63 microns may be determined using an optical microscopy technique or laser techniques as known in the pertinent art. Particle size measurements for particles having a particle size of at most 63 microns may be determined using a hydrometer method as defined by ASTM D422. In one or more embodiments, the mineral fines may have a mono-modal particle size distribution. In one or more other embodiments, the mineral fines may have a multi-modal particle size distribution, for example bi-modal, tri-modal, etc. The particle size measurements may be based from Wentworth grain size classification. See, e.g., Wentworth, C. K., 1922, A scale of grade and class terms for clastic sediments: Journal of Geology, v. 30, p. 377-392.

In one or more embodiments, the dosage rate for surface application of mineral fines to promote oil dispersion may include 1 part mineral fine to 1 parts oil (by weight) to 1 part mineral fine to 5 parts oil (by weight) may be utilized. The dosage rate for subsea application of mineral fines to promote oil dispersion may be 10 times or more lower from 1 part mineral fine to 5 parts oil (by weight) to 1 part mineral fines to 50 parts oil (by weight).

In one or more embodiments, the method for managing a hydrocarbon release with a hydrocarbon release management system may also including identifying a source for mineral fines near the hydrocarbon release, which may include the use of an underwater vehicle. The method may include positioning dredging equipment (optionally, with the underwater vehicle) and operating the dredging equipment to obtain the mineral fines. The method may also include positioning injection equipment (optionally, with the underwater vehicle) near the hydrocarbon release and injecting the mineral fines into the hydrocarbon plume resulting from the hydrocarbon release via the injection equipment. The method may further include adjusting one or more of the injection equipment and/or the dredging equipment based on the measurement determination of the characteristics of the hydrocarbon plume.

In one or more embodiments, determining whether to adjust the injection operations may include determining droplet sizes in the hydrocarbon plume using a droplet size sensor; determining hydrate generation within the hydrocarbon plume; comparing the characteristics of the hydrocarbon plume over a period of time; and/or comparing images of the hydrocarbon plume over a period of time. Comparison of characteristics and/or images may be of characteristics or images of the hydrocarbon plume prior to injection of mineral fines to one or more subsequent characteristics or images of the hydrocarbon plume or may be between two or more subsequent characteristics or images after injection of mineral fines.

Beneficially, using mineral fines as a dispersant for subsea hydrocarbon releases may provide certain enhancements to the management of hydrocarbons. For example, the sediments that are present in most deepwater environments provide an abundant in situ supply of mineral fines for hydrocarbon release operations. Also, using mineral fines as a dispersant for subsea hydrocarbon releases eliminates and/or reduces the cost and resupply challenges associated with chemical dispersant stockpiles, as the mineral fines may be collected near the hydrocarbon release location as a substitute or supplement to the injection of chemical dispersants. In addition, using mineral fines as a dispersant for subsea hydrocarbon releases eliminates and/or reduces the logistical challenges of transporting chemical dispersants or mineral fines to offshore locations during a hydrocarbon release. Further, the mineral fines may "catalyze" the formation of natural gas hydrates. Forming hydrates proximate the point of the release changes the buoyancy of the plume of oil and also reduces the potential for natural gas to reach the surface, which may be near the well-control operations. That is, this technique may provide further enhancements to the protection of the health and safety of responders.

In one or more embodiments, the hydrocarbon release management system may also include a command unit that may include a computer system comprising: a processor; memory in communication with the processor; and a set of instructions stored on the memory and accessible by the processor, wherein the set of instructions, when executed, are configured to: receive the transmitted signal from one or more sensors; determine the characteristics of the hydrocarbon plume based on the transmitted signal; and provide a visual indication of the effectiveness of the dispersion of the hydrocarbon plume based on the determination.

In one or more embodiments, an underwater vehicle may be utilized with the system, wherein the underwater vehicle may be configured to position one or more of the dredging equipment and/or the injection equipment. The underwater vehicle may be in communication with the command unit and have a propulsion component, a communication component and measurement modules, wherein the measurement modules may be configured to measure the characteristics of the hydrocarbon plume and the communication component may be configured to communicate signals associated with the measured characteristics of the hydrocarbon plume to the command unit. The measurement modules may include a camera (e.g., a high definition camera) attached to a retractable line; a sampling tube; a droplet size sensor; a hydrate sensor and/or a Sonar system.

In one or more embodiments, the method for managing a hydrocarbon release (e.g., a well control event) may include one or more vessels configured to collect and transfer mineral fines to a hydrocarbon release. The method may include outfitting a response vessel for collecting seabed sediments (e.g., mineral fines) in the vicinity of a hydrocarbon release (e.g., a well releasing oil and/or gas near the seabed), transferring the collected sediments to the injection equipment and injecting the collected sediments into the flowing discharge of oil and/or gas. In one or more embodiments, the method may additionally include separating the collected sediments to remove particle sizes outside of the desired range for the mineral fines. Any suitable separator may be used which is capable of separating out the desired particle size of the mineral fines, for example a sieve-based shaker table commonly used in drilling operations could be used. This shaker table could be placed on a surface vessel or operated on the seabed. The injection of collected sediments may be within the discharge orifice or adjacent the discharge orifice in the turbulent jet of oil and/or gas.

Subsea dredging or sediment collection equipment can be used to continuously transport and accumulate fine sediments in the vicinity of the mineral fines injection. This approach may be utilized to provide a continuous supply of material without interruption to injection operations. The pump and tubing which may be used to mobilize and inject the fine sediments into the plume may be operated from the sea bottom or from a vessel at the water surface.

The present techniques may also include a method for deploying and positioning subsea equipment for retrieval of sea floor sediments (e.g., mineral fines, which may include a desired particle size) and injecting the mineral fines into a subsea hydrocarbon plume to promote oil dispersion. As may be appreciated, the equipment may include various different components to manage the process.

For example, the method and system may include one or more marine vessels (e.g., work boats) that include one or more underwater vehicles (UV) (e.g., remotely operated vehicles (ROVs) or autonomous underwater vehicle (AUV)), one or more injection equipment and one or more subsea dredging equipment. The one or more UVs may be deployed to the sea floor in the region near the subsea hydrocarbon discharge (e.g., the hydrocarbon release location). Then, the dredging equipment and injection equipment may be lowered to the sea floor near the UV(s). The UVs may be utilized to and/or configured to: i) identify a suitable source of sediment; ii) position the dredging equipment such that the intake end of the dredging hose may be positioned proximate a suitable source of sediment (e.g., mineral fines to be injected into the hydrocarbon release); and iii) position injection equipment (e.g., a pump outlet) in the direction of the hydrocarbon plume near the discharge location. The UV may also be configured to control the location of the intake element of the dredging equipment (e.g., a hose or other tubular member) at the sea floor to collect sediment and to move the intake element as necessary to facilitate continuous collection and injection operations.

Further, the system may include one or more sensors, which may be mounted on an UV, injection equipment and/or the dredging equipment and used to monitor effective delivery of the mineral fines into the hydrocarbon release and to assess the dispersion effectiveness. The one or more sensors may communicate with the UV, which may manage the operation of the injection equipment and/or the dredging equipment (e.g., in an automated manner), may communicate with a control unit on the marine vessel, and/or may communicate with another control unit.

Additional configurations may include more than one UV, injection equipment and/or dredging equipment. For example, dredging equipment may be deployed in the region of operations to collect sediment and transport the sediment to a sea floor stockpile adjacent to the hydrocarbon release location. The injection equipment (e.g., a pump and hose configuration) may then pump mineral fines from the seafloor stockpile into the plume. This configuration may include two or more dredging equipment locations to provide a mechanism to collection mineral fines at multiple locations. In this manner, the collection operations may be scaled up as needed to provide an adequate supply of mineral fines for the injection equipment. Further, in another configuration, dredging equipment and injection equipment may be arranged in a one to one configuration such that one to one configurations may be distributed at different locations relative to the hydrocarbon release location. In this manner, the mineral fines may be injected into the hydrocarbon release (e.g., the hydrocarbon plume) at different orientations to further enhance the process. Various aspects of the present techniques are described further in FIGS. 1 to 2.

FIG. 1 is flow chart 100 for performing oil release management in accordance with one or more embodiments of the present disclosure. The hydrocarbon management system may include one or more underwater vehicles (UV), such as a remotely operated vehicle (ROV) or an autonomous underwater vehicle (AUV), one or more injection equipment; one or more subsea dredging equipment and/or one or more sensors. In this flow chart 100, the method includes various stages, which include a preparation and deployment stage, which includes blocks 102, 104, 106 and 108, followed by an operation stage, which includes blocks 110, 112, 114, 116 and 118.

The process begins with the preparation and deployment stage, which prepares the equipment and deploys the equipment to the hydrocarbon release location. The process begins at block 102 by providing a hydrocarbon management system. The hydrocarbon management system may include one or more underwater vehicles (UVs), one or more injection equipment; one or more subsea dredging equipment and/or one or more sensors. In one or more embodiments, the system may include the operation of a remotely operated vehicle (ROV), injection equipment and dredging equipment. However, as may be appreciated, the hydrocarbon management system may be configured for various combinations of these components.

Block 104 includes transporting at least a portion of the hydrocarbon management system near the hydrocarbon release location. This may include using a marine vessel to move the underwater vehicle (UV), injection equipment and dredging equipment to a deployment location near the hydrocarbon release location. The transporting may include fueling the marine vessel, loading the equipment onto the marine vessel and moving the marine vessel from a port location to the deployment location. Then, at block 106, equipment is deployed from the deployment location to a location near the hydrocarbon release location. The deployment of equipment may include moving the UV, injection equipment and dredging equipment from the marine vessel to a suitable location near the hydrocarbon release location. The deployment may include launching the UV and using the UV to identify a source of mineral fines. The identification may include locating a mineral fines source with sediment of the appropriate size and quantity. Once a source of mineral fines is identified, the dredging equipment may be deployed to the identified source location, while the injection equipment may be deployed to a location adjacent to the hydrocarbon release location. Once deployed, the equipment may be positioned for the injection operations, as shown in block 108. The positioning of the equipment may include using the UV to move the dredging equipment near a source of mineral fines and positioning the injection equipment to be directed at the hydrocarbon plume. That is, the UV may adjust hoses and/or nozzles to orient the injection stream of mineral fines into the hydrocarbon plume. As may be appreciated, the UV may perform other operations as part of the deployment process. As may also be appreciated, the source of mineral fines may include mineral fines obtained from a remote location and transported to the hydrocarbon release location. The remote source of mineral fines may provide substantially all the required mineral fines or may supplement mineral fines obtained from a location near the hydrocarbon release.

After the preparation and deployment stage, the operation stage is performed, as noted in blocks 110, 112, 114, 116 and 118. In block 110, the mineral fines are injected into the hydrocarbon plume. The injection may include further refinement of the positioning of the injection equipment near the hydrocarbon plume such that the mineral fines are injected directly into the hydrocarbon plume at the release point or partially into the hydrocarbon plume as near the release point as possible (e.g., adjacent to the release point) or even partially or fully inside the release point before the hydrocarbon expels into the marine environment and forms a plume.

At block 112, the injection of mineral fines into the hydrocarbon plume may be monitored. The monitoring may include observing the behavior of the hydrocarbon plume as it travels further into the marine environment or using a sensor to detect a change in or more parameters the hydrocarbon plume after injection of the mineral fines (e.g., visual observations that involve infrared or visible light detection, for example). This may involve controlling the one or more other UVs or other sensors to different locations and obtain measurements associated with the hydrocarbon plume. Sensors may be used to detect a change in hydrocarbon droplet size within the plume after injection of mineral fines, to detect the formation of hydrates after injection of mineral fines, and/or to detect a change in plume trajectory after injection of mineral fines. The system may include one or more sensors, which may be mounted on an UV, injection equipment and/or the dredging equipment and used to monitor effective delivery of the mineral fines into the hydrocarbon plume and to assess the dispersion effectiveness. The one or more sensors may communicate with the UV, which may manage the operation of the injection equipment and/or the dredging equipment (e.g., in an automated manner), may communicate with a control unit on the marine vessel, and/or may communicate with another control unit. Further, the sensors may be configured to collect and transmit information within a set time window (e.g., every 10 seconds, 60 seconds, 5 minutes, or even 10 minutes), transmit information when polled by the command unit, or transmit information after each measurement has been collected.

The monitoring or measurement of the hydrocarbon plume may include positioning the sensor within or near the hydrocarbon plume and performing one or more of the measurement techniques. These measurement techniques may include one or more different measurement modules utilized by the sensor to determine the dispersion of the hydrocarbon plume. These measurement techniques may include deploying one or more particle size analyzing sensors into the hydrocarbon plume a distance of one or more meters above the point of injection of mineral fines, two or more meters above the injection point, five or more meters above the injection or ten or more meters above the injection point before initiation of the mineral fines injection. This provides a mechanism to determine the hydrocarbon droplet sizes in the hydrocarbon plume before initiation of mineral fines injection. Subsequently, the same equipment may be used to measure the hydrocarbon droplet size distribution after injection of mineral fines. A significant reduction in the particle size provides evidence that the mineral fines are breaking the hydrocarbons into dispersed droplets as desired.

In another measurement technique, one or more hydrate detecting sensors may be placed into the hydrocarbon plume a distance of one or more meters above the point of injection of mineral fines, two or more meters above the injection point, five or more meters above the injection or ten or more meters above the injection point before initiation of the mineral fines injection. The sensor may be activated to monitor hydrate formation before and after initiating of mineral fines injection to determine if injection of mineral fines significantly changes the amount of hydrates formed.

In yet another measurement technique, an open-ended sample cylinder is initially positioned into the hydrocarbon plume, the sample cylinder ends are then closed via a remote actuating device, the tube is retracted from the hydrocarbon plume. An image of the tube may be obtained to determine the adequacy of sample collection.

Further, another measurement technique may include positioning an imaging camera to photograph the hydrocarbon plume. The camera captures the image in the visible, infrared or other suitable wavelength to determine visual changes in the plume before and after mineral-fine injection.

In yet another measurement technique, a sonar system is positioned one or more meters above the point of injection of mineral fines, two or more meters above the injection point, five or more meters above the injection or ten or more meters above the injection point before initiation of the injection of mineral fines injection. The sonar system can image the plume travel path before and after injection of mineral fines to determine if the plume trajectory has changed.

Once the measurement(s) have been obtained, a determination is made whether to adjust the injection operations, as shown in block 114. The determination may involve adjusting the injection rate of mineral fines into the hydrocarbon plume, adjusting the source of mineral fines, adjusting the orientation of the injection stream into the hydrocarbon plume, adjusting the location of the injection system, and other suitable operations. In one or more embodiments, the UV may move the intake hose to maintain a continuous supply of mineral fines or adjust the location of the injection hose to position it more closely to the hydrocarbon discharge point or within the hydrocarbon discharge point.

A determination is then made whether to cease the injection operations, as shown in block 116. This determination may include determining if the hydrocarbon plume is dissipating or if injection operations should cease to allow other operations to be performed on the hydrocarbon release location. If the operation is not complete, the method continues to monitor the injection of mineral fines into the hydrocarbon plume as noted in block 112.

If the operation is complete, the deployed equipment is recaptured, as shown in block 118. The recapture of equipment may include moving the UV, injection equipment and dredging equipment from the suitable location near the hydrocarbon release location to the marine vessel. The deployment may include recovering the UV and using the UV to recover the other equipment.

Figure 2:
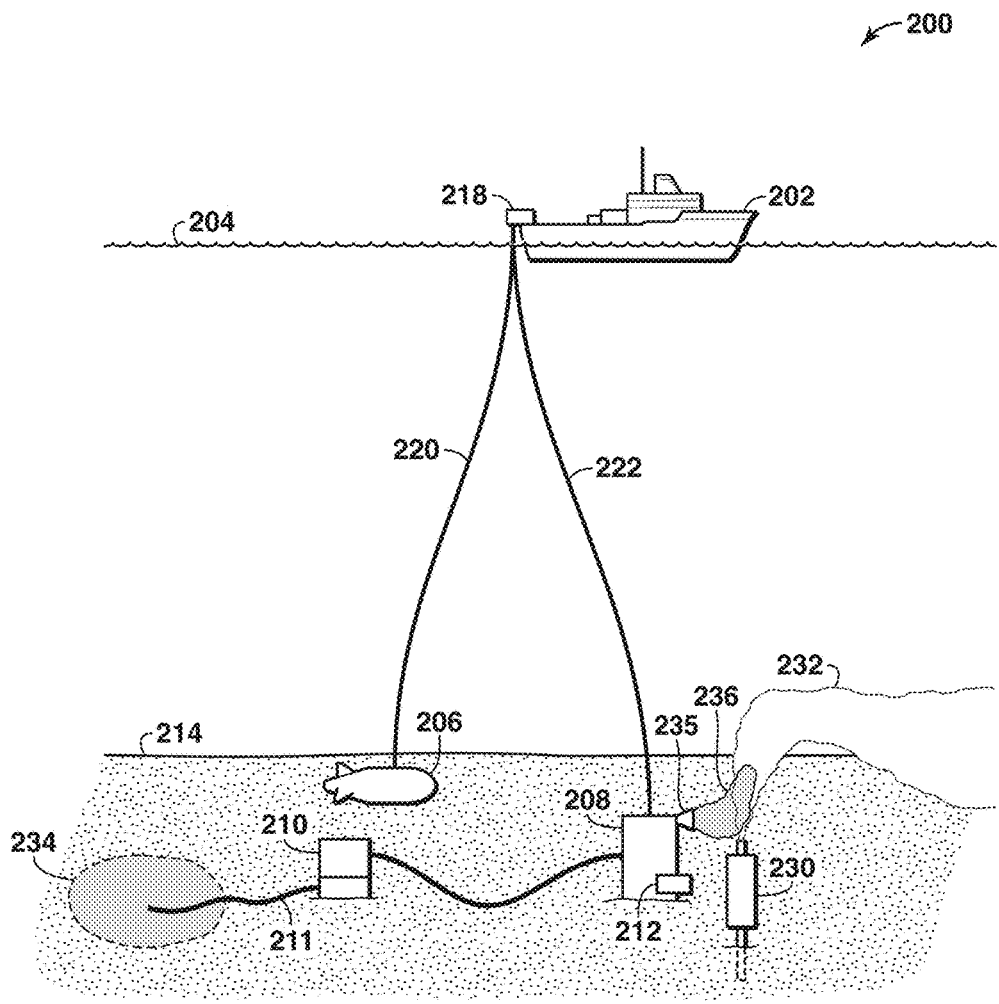
FIG. 2 is a diagram of a hydrocarbon release management system in accordance with one or more embodiments of the present disclosure.

FIG. 2 is a diagram of a hydrocarbon release management system 200 in accordance with one or more embodiments of the present disclosure. This diagram illustrates how the equipment and marine vessel may be positioned for injection operations. The hydrocarbon release management system 200 may include a marine vessel 202 positioned on the surface of a body of water 204 along with an underwater vehicle (UV) 206, injection equipment 208; subsea dredging equipment 210 and/or one or more sensors 212 disposed above the sea floor 214. In this configuration, the hydrocarbon release location is the area around a subsea well 230, which is releasing a hydrocarbon plume 232. The subsea dredging equipment 210 obtains mineral fines from the mineral fines source 234, and these are transported to the injection equipment 208 for injection of the mineral fines (mineral fines stream 236) into the hydrocarbon plume 232.

The mineral fines source can be identified visually using a video camera on the UV. The sediments of the correct size are readily discerned visually based on how easily they are disturbed by the thrusters on the UV. A trained UV operator can make this determination. Alternatively, the mineral fines may be identified by separating and measuring the sediments at various locations to determine distribution of mineral fines at the locations. This may involve differentiating the sea floor material by dredging, separating and/or other techniques to analyze the sea floor materials. The identification may differentiate sand, silt and/or clay sediments.

In one or more embodiments, the marine vessel 202 may be an oil spill response or well control work boat outfitted with the underwater vehicle (UV) 206, injection equipment 208 and subsea dredging equipment 210. The UV 206 may be deployed to locations near the sea floor 214 in the region of the subsea hydrocarbon discharge (i.e., the hydrocarbon release location at the subsea well 230 which is the source of the hydrocarbon plume 232). The dredging equipment 210 may be lowered to the sea floor 214 at a location proximate to the UV 206. The UV 206 is used to position the dredging equipment 210 such that the intake end of the dredging hose 211 is positioned proximate the source sediment (i.e., mineral fines source 234 that is to be applied to the hydrocarbon plume 232). The UV 206 may also be used to position the nozzle 235 (e.g., located at a pump outlet within the injection equipment 208) in an orientation toward the hydrocarbon plume 232 near the hydrocarbon release location. The UV 206 may also be used to hold the intake end of the hose 211 at the sea floor 214 to collect sediment and to move the hose 211 as necessary to facilitate continuous collection/injection operations. Underwater sensors, such as sensor 212 mounted on the injection equipment 208, are utilized to monitor effective delivery of the mineral fines (e.g., via the mineral fines stream 236) into the hydrocarbon plume 232 and to assess the dispersion effectiveness. The sensors (not shown) may also be mounted on the UV 206, anchored to the sea floor 214 or mounted on a separate component and independently operated, as well. Sensors may be mounted on a separate UV and located adjacent to the hydrocarbon plume 232.

Additional configurations may include two or more of the different units. In one or more embodiments, the dredging equipment may include two or more dredging units deployed in different source regions to collect sediment (e.g., mineral fines) and transport the mineral fines to a sea floor stockpile adjacent to the injection equipment. The injection equipment may then pump mineral fines from the seafloor stockpile into the hydrocarbon plume. This approach provides scaling of the collection operations as needed to provide adequate mineral fines to the injection equipment. As another example, the injection equipment may include two or more injection units. These different injection units may be utilized to provide mineral fines stream at different orientations to further enhance intermingling of the mineral fines with the hydrocarbon plume. In one or more embodiments, two or more UVs may be utilized to further enhance the operations. In particular, one UV may be utilized to adjust the injection equipment, while the second UV is utilized to manage the dredging equipment.

In one or more embodiments, the marine vessel 202, underwater vehicle (UV) 206, injection equipment 208; subsea dredging equipment 210 and/or one or more sensors 212 may include power components, communication components and/or management components. These different components may be utilized to enhance the operations in a variety of configurations.

Each of the marine vessel 202, underwater vehicle (UV) 206, injection equipment 208; subsea dredging equipment 210 and/or one or more sensors 212 utilize power to operate. The power components may be separate and dedicated to each of these different units, may be shared between the different units or any combination thereof. Also, the different components and modules may also utilize a separate power source as a redundant power supply in certain embodiments. In FIG. 2, the marine vessel 202 has a power component that supplies power to components on the marine vessel, the UV 206 via cable 220, and the subsea dredging equipment 210 (not shown). The power components for the UV 206 and marine vessel 202 may also be utilized for propulsion and to operate various components disposed on the respective vessel. The propulsion may be provided by a propulsion component, which is utilized to maneuver the UV 206 and the marine vessel 202. The power components may include a battery and/or solar powered equipment.

The communication components may include communication equipment that is utilized with one or more marine vessel 202, underwater vehicle (UV) 206, injection equipment 208; subsea dredging equipment 210 and/or one or more sensors 212 to communicate with one or more of the units and/or the command unit 218. The communication components may include communication equipment that is utilized with one or more antennas to communicate with one or more of other units, internal components or modules, and/or the command unit 218. The communication equipment may utilize technologies, such as radio, cellular, wireless, microwave or satellite communication hardware and software. Also, the communication equipment may include and utilize any of a variety of known protocols to manage the exchange of information (e.g., Ethernet, TCP/IP, and the like). The communication equipment utilized may depend on the specific deployment locations and configuration.

In one or more embodiments, the command unit 218 may be disposed on the marine vessel 202 and operate as a hub for communication and interaction with the UV 206, the injection equipment 208 and the sensors 212. The subsea dredging equipment 210 may communicate via the UV 206 and/or injection equipment 208. In one or more embodiments, the UV 206, injection equipment 208; subsea dredging equipment 210 and/or one or more sensors 212 may be in communication via cables with a command unit 218, which is disposed on the marine vessel 202. The communication may involve the transmission of commands and monitoring data between the equipment and the command unit 218. In one or more embodiments, the UV 206 is coupled to the command unit 218 via cable 220, which is utilized to control the operation of the UV 206 in performing various operations from the marine vessel 202. In one or more embodiments, the injection equipment 208 is coupled to the command unit 218 via equipment cable 222, which may also supply power to injection equipment 208.

The management components may include different modules, which may include hardware, sets of instructions stored in memory and configured to be accessed by a processor to execute the set of instructions, or a combination of both. These modules may include a display and imaging module that present the images or visual indications to an operator, and modules configured to operate measurement components deployed to monitor the hydrocarbon plume 232 or the mineral fines source 234. The management components may include different measurement modules to perform one or more of the measurement techniques. These may include one or more high definition ("HD") cameras, infrared ("IR") cameras, wench components (to secure and hold objects) and other suitable equipment. The measurement components may include one or more open ended sample tubes mounted on a retractable line, cameras mounted on a retractable line, sensors to monitor hydrocarbon particle size in the plume, sonar equipment, sensors to measure hydrate formation, and/or a conductivity probe mounted on a retractable line.

Persons skilled in the technical field will readily recognize that in practical applications of the disclosed methodology (e.g., the operation of the management components, communication components, measurement modules and other components utilized in these operations), it may be partially performed on a computer, typically a suitably programmed digital computer. Further, some portions of the disclosure are presented in terms of procedures, steps, logic blocks, processing and other symbolic representations of operations on data bits within a computer memory. These descriptions and representations are the mechanisms used by those skilled in the data processing arts to most effectively convey the substance of their work to others skilled in the art. In the present disclosure, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing the terms such as "processing" or "computing", "calculating", "determining", "displaying", "copying," "producing," "storing," "adding," "applying," "executing," "maintaining," "updating," "creating," "constructing" "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present disclosure also relate to an apparatus for performing the operations herein. This apparatus may be specially constructed for the required purposes, or it may comprise a general-purpose computer selectively activated or reconfigured by a computer program stored in the computer (e.g., one or more sets of instructions). Such a computer program may be stored in a computer readable medium. A computer-readable medium includes any mechanism for storing or transmitting information in a form readable by a machine (e.g., a computer). For example, but not limited to, a computer-readable (e.g., machine-readable) medium includes a machine (e.g., a computer) readable storage medium (e.g., read only memory ("ROM"), random access memory ("RAM"), magnetic disk storage media, optical storage media, flash memory devices, etc.), and a machine (e.g., computer) readable transmission medium (electrical, optical, acoustical or other form of propagated signals (e.g., carrier waves, infrared signals, digital signals, etc.)).

Furthermore, as will be apparent to one of ordinary skill in the relevant art, the modules, features, attributes, methodologies, and other aspects of the present disclosure may be implemented as software, hardware, firmware or any combination of the three. Of course, wherever a component of the present disclosure is implemented as software, the component may be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present disclosure is in no way limited to implementation in any specific operating system or environment.

Further, one or more embodiments may include methods that may be performed by executing one or more sets of instructions to perform operational enhancements in various stages. For example, the method may include executing one or more sets of instructions to perform monitoring the dredging operation, the injection operations, and the plume measurement operations.

A computer system may be utilized and configured to implement one or more aspects of the present disclosure. The computer system may include a processor; memory in communication with the processor; and a set of instructions stored on the memory and accessible by the processor, wherein the set of instructions, when executed, are configured to: receive the transmitted signal from one or more of an underwater vehicle (UV), injection equipment; subsea dredging equipment 210 and/or one or more sensors; determine changes in the hydrocarbon plume based on the transmitted signal; and provide a visual indication of the dispersion in the hydrocarbon plume based on the determination. Further, the determination of the changes in the hydrocarbon plume based on the transmitted signal may comprise a set of instructions, when executed, configured to: compare images of the hydrocarbon plume; and display on a monitor the effectiveness of the dispersion based on this comparison. Comparison of images may be of the hydrocarbon plume prior to injection of mineral fines to one or more subsequent images of the hydrocarbon plume (e.g., the most recent image of the current plume) or may be between one or more subsequent images after injection of mineral fines, one of which may be the most recent image of the current plume. Further, the determination of the effectiveness of the dispersion based on the transmitted signal may comprise a set of instructions, when executed, configured to: compare subsequent sensor readings (e.g., the current sensor readings) to readings collected prior, for example before initiation of mineral fines injection. The display to the monitor may include changing the color of the plume as presented based on the effectiveness of the dispersion operations. As an example, the display may include changing the color of the plume from red for the initial state to yellow for 5% to 50% dispersion and to green for 50% to 100% dispersion.

In one or more embodiments, the command unit may include a set of instructions stored on the memory and accessible by the processor, wherein the set of instructions, when executed, are configured to provide one or more of a visual indication and audible notification associated with the status of the hydrocarbon plume. Also, the command unit may include a set of instructions stored on the memory and accessible by the processor, wherein the set of instructions, when executed, are configured to store hydrocarbon plume status at the specific location.

Figure 3:
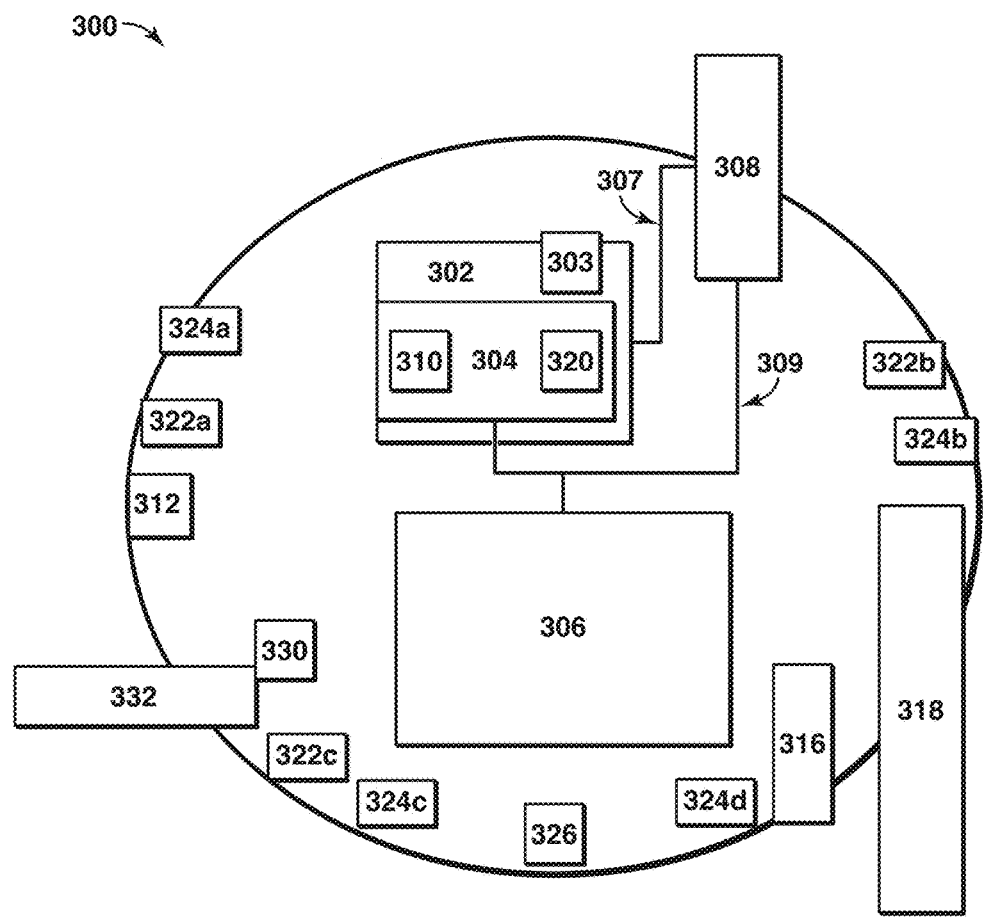
FIG. 3 is a diagram of an automated underwater vehicle in accordance with one or more embodiments of the present disclosure.

As may be appreciated, the underwater vehicle may include different configurations and methods of operation which may include various different combinations of components to be able to operate. FIG. 3 is a diagram of a remotely operated vehicle (ROV) 300 in accordance with one or more embodiments of the present disclosure. In this ROV 300, a process control unit 302 is utilized to manage the components or modules for navigation, measurement, and manipulation. The process control unit 302 includes a processor 303, memory 304 and sets of instructions (e.g., master navigation module 310 and master measurement module 320) that are stored in the memory 304 and executable by the process control unit 302. The power for the process control unit 302 may be supplied by one or more batteries 306 or by an electrical connection to a power supply located on the surface vessel 202. Also, the process control unit 302 may include a communication component 308, which may include an antenna and other equipment to manage communications with other systems, such as marine vessel and/or GPS.

The navigation components of the ROV 300 may include the master navigation module 310, a mapping component, such as SONAR component 312, motion sensor component 316 and propulsion component 318. The master navigation module may operate by the processor executing the sets of instructions configured to: manage the different navigation components, calculate the path of the ROV, obtain signals (e.g., GPS signals and/or wireless guidance signals), communicate with the propulsion systems to adjust steering and/or speed of the ROV, obtain motion sensor data, and/or calculate the ROV's location based on different data (e.g., GPS data, wireless guidance data, motion sensor data and mapping component data). The SONAR component 312 may include SONAR sensor equipment to send and receive SONAR signals and provide associated SONAR data to the master navigation module. The SONAR component 312 may also be utilized for the detection of hydrocarbons external to the ROV (e.g., in fluid disposed external to the ROV, such as a body of water that the ROV is disposed within). The motion sensor component 316 may include various sensors and other equipment to obtain motion sensor data about the forces applied to the ROV 300 (e.g., currents and fluid flows). The motion sensor component 316 may include a processor that communicates with a gyroscope, depth sensor, velocity meter along with various other meters to measure the orientation or other parameters of the ROV. Also, the propulsion component 318 may include two propeller assemblies enclosed by a propeller support members, a motor coupled to the batteries 306.

The measurement modules of the ROV 300 may include the master measurement module 320, resistivity components 322a-322c, camera component 324a-324d and/or other hydrocarbon detection component 326 along with the SONAR component 312. The master measurement module may operate by the processor executing the sets of instructions configured to: manage the different measurement modules, determine the droplet size in the hydrocarbon plume using an appropriate instrument such as a droplet size sensor (e.g., droplet size sensor the LISST Deep manufactured by Sequoia Instruments); the generation of hydrates within the hydrocarbon plume using high-definition cameras, communicate with the propulsion systems to adjust steering and/or speed of the ROV based on operations being performed, obtain measurement data and the ROV's location based on different indications, and store certain measurement data and ROV location data. The camera components 324a-324d may include various cameras that are configured to obtain images (e.g., the images may be subjected to different filters) of the hydrocarbon plume or the source of mineral fines and provide these images to a processor, which is configured to send and receive commands, process the images, and to communicate the camera data and/or certain notifications with the master measurement module 320. The other hydrocarbon detection components 326 may also include a processor configured to send and receive commands, to process the measured data, and to communicate measured data and/or certain notifications with the master measurement module 320.

The manipulation components of the ROV 300 may include the master manipulation module 330 and a manipulation element 332. The master manipulation module 330 may operate by the processor executing the sets of instructions configured to: move the manipulation element 332 into different positions and orientations, secure objects with the manipulation element 332 (e.g., by grasping the objects or using magnets to secure an object), communicate with the propulsion systems to adjust steering and/or speed of the ROV based on operations being performed, and adjust the position of objects.

The equipment within the ROV 300 may be coupled together through physical cables to manage the distribution of power from the batteries 306 and to manage communication exchanges between the equipment. As an example, power distribution is provided between the process control unit 302, the one or more batteries 306 and the communication component 308 via lines 309, while the communication distribution is provided between the process control unit 302 and the communication component 308 via line 307. Other communication and power distribution lines are not shown for simplicity in this diagram. Also, the communication between certain devices may be via wireless communications, as well. Accordingly, the specific configuration with the ROV provides flexibility.

As noted above, various methods of performing measurements may be used to determine hydrocarbon droplet sizes in the hydrocarbon plume, hydrate formation in the hydrocarbon plume, collect samples of the hydrocarbon plume with sample cylinders, and image the hydrocarbon plume with Sonar in accordance with one or more embodiments of the present disclosure. For simplicity, each of these flow charts describes the use of an underwater vehicle along with dredging equipment and injection equipment. As may be appreciated, this equipment may be combined into a single unit or distributed into various units depending on the specific application. Further, the UV may be remotely controlled by an operator on a marine vessel or may be autonomously operated. The sensors in this system may include high definition (HD) and infrared (IR) cameras, laser particle size analyzers, hydrate detection systems, and Sonar that transmit these signals to a command unit on the marine vessel.

The method of performing measurements with a sample analysis module in accordance with one or more embodiments of the present disclosure may include one or more clear sample cylinders that may be attached to the UV. The sample tubes may be open at each end, but the ends may be closed remotely to seal the tube. The UV may be positioned at an appropriate distance from the hydrocarbon plume to avoid disturbing the hydrocarbon plume. The sample tube is positioned into the hydrocarbon plume until it is at least partly disposed in the hydrocarbon plume. This could be facilitated by placing the tube in a buoyancy device that causes it to float in the proper location. At this point, both ends of the sample tube are closed and the sample tube is removed from the hydrocarbon plume. Once out of the plume, an image is taken of the tube using the HD camera on the UV to assess the adequacy of the sample collection and the tube may be returned to a sample holding container on the UV.

This process may begin by first placing the one or more sample holding containers each containing one or more sampling tubes onto the UV while it is located on the marine vessel 202. Once installed, the UV is lowered towards the seabed to a position allowing it to maneuver a sampling tube until it is at least partially into the hydrocarbon plume. Once in position, the command unit sends a command via the process control unit 302 to the UV instructing it to remove an empty sample tube from the sample holding container and place it until it is at least partially into the hydrocarbon plume. The command unit then sends a command via the process control unit 302 to the UV instructing it to trigger the mechanism to force each end of the open sampling tube to a closed position. Once the ends close, the UV maneuvers the sampling tube out of the hydrocarbon plume and the command unit instructs the HD camera to collect an image of the sampling tube. The image is then transferred back to the command unit for storage and visual display. The command unit may assess the quality of the sample collection and the UV is then instructed to place the sampling tube into the sample holding container. This process is repeated as desired by the command unit to collect more than one sample at the same location or the command unit can instruct the UV to move to another location for collection of a sample.

Another method may include performing measurements with a camera analysis module in accordance with one or more embodiments of the present disclosure. This method involves placing an imaging camera and/or an infrared camera on the UV. The camera(s) may be set up in a configuration to photograph the hydrocarbon plume. It may also be set up in a configuration that allows the lens to be cleared of contaminants between sampling and/or imaging at the different locations. The UV positions the camera module an appropriate distance from the hydrocarbon plume to avoid having the UV disturb the hydrocarbon plume. The camera is positioned into the hydrocarbon plume so that the lens can image the entire width of the plume or the lens can zoom in to image only a section of the plume. This imaging is collected downstream of the mineral fines injection location before and after initiation of injection. The images may be sent to the command unit so they may be visually compared before and after initiation of mineral fines injection to determine if a significant change in the visual character of the plume has occurred. The comparison of images may also involve determining changes in the backscatter image from Sonar (an indication of reduced droplet size), change in trajectory of the plume based on visual or IR images. Further, the images may be compared to changes in the surface expression of the oil from satellite or aerial images.

This process begins by first placing the one or more Sonar, HD and/or IR cameras onto the UV while it is located on the marine vessel 202. Once installed, the UV is lowered towards the seabed to a position allowing it to maneuver the cameras to an appropriate location adjacent to hydrocarbon plume. Once in position, the command unit sends a command via the process control unit 302 to the Sonar, HD and/or IR cameras instructing them to collect an image of at least a portion of the hydrocarbon plume. The image(s) may then be transferred back to the command unit for storage and visual display. This process may be repeated as desired by the command unit to collect more than one image at the same location or the command unit may instruct the UV to move to another location for collection of a different image.

Another method may include performing measurements with a hydrocarbon droplet size analysis module in accordance with one or more embodiments of the present disclosure. This method utilizes one or more droplet size sensors (e.g., suitable particle size sensors mounted onto one or more UVs). The UV may be used to maneuver the droplet size sensor directly into the hydrocarbon plume downstream of the mineral fines injection point. The droplet size sensor then continuously monitors the particle size distribution of hydrocarbon droplets passing through its sampling chamber. The droplet size sensor should be placed into the hydrocarbon plume before and after mineral fines injection to determine the change in hydrocarbon droplet sizes.

This process begins by first placing the one or more droplet size sensors onto the UV while it is located on the marine vessel 202. Once installed, the UV may be lowered towards the seabed to a position allowing it to maneuver the droplet size sensor at least partially into the hydrocarbon plume. Once in the plume, the command unit sends a command via the process control unit 302 to the droplet size sensor instructing the droplet size sensor to begin data collection. The droplet size sensor then begins measuring the particle size distribution of hydrocarbon droplets that pass through its sampling port. The data describing the hydrocarbon droplet size distributions is then transferred back to the command unit for storage and visual display. The collection of hydrocarbon droplet sizes using the droplet size sensor may either be continuous and terminate after cessation of mineral fines injection or it may be intermittent and switched on and off as desired by the command unit.

As yet another technique, a method of performing measurements with a hydrate sample analysis module may be utilized. The method utilizes one or more hydrate sensors mounted onto one or more UVs. The UV may be used to maneuver the hydrate sensor into an appropriate location either within or near the hydrocarbon plume downstream of the mineral fines injection point. The hydrate sensor may then continuously monitor the formation of hydrates within the hydrocarbon plume. The hydrate sensor should be placed into the hydrocarbon plume before and after mineral fines injection to allow the change in hydrate formation to be determined.

This process begins by first placing the one or more hydrate sensors onto the UV while it is located on the marine vessel 202. Once installed, the UV may be lowered towards the seabed to a position allowing it to maneuver the hydrate sensor to an appropriate location to measure hydrates within the plume. Once in the appropriate location, the command unit sends a command via the process control unit 302 to the hydrate sensor instructing the hydrate sensor to begin data collection. The hydrate sensor then begins measuring the concentration of hydrates within the hydrocarbon plume. The data describing the hydrate concentration is then transferred back to the command unit for storage and visual display. The collection of hydrate concentration using the hydrate sensor may either be continuous and terminate after cessation of mineral fines injection or it may be intermittent and switched on and off as desired by the command unit.

In still yet another technique, a method of performing measurements with a Sonar sample analysis module may be utilized. The method utilizes one or more Sonar systems mounted onto one or more UVs. The UV is used to maneuver the Sonar sensor to a position adjacent, but outside the hydrocarbon plume downstream of the mineral fines injection point. The Sonar system may then generate a Sonar image of the hydrocarbon plume based on Sonar backscatter measurements, which may be continuous or based on a sampling interval. The UV may maneuver the Sonar system to various locations downstream of the mineral fines injection point to collect multiple Sonar images of the plume. The Sonar system should be placed into the hydrocarbon plume before and after mineral fines injection to provide the change in Sonar images to be determined.

This process begins by first placing the one or more Sonar systems onto the UV while it is located on the marine vessel 202. Once installed, the UV may be lowered towards the seabed to a position that provides it the flexibility to maneuver the Sonar system to an appropriate location to obtain a Sonar backscatter image of the plume. Once in the appropriate location, the command unit sends a command via the process control unit 302 to the Sonar system instructing it to begin data collection. The Sonar system then begins collecting backscatter images of the hydrocarbon plume. The Sonar backscatter images are then transferred back to the command unit for storage and visual display. The collection of Sonar backscatter images using the Sonar system may either be continuous and terminate after cessation of mineral fines injection or it may be intermittent and switched on and off as desired by the command unit.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

What is claimed is:
1. A method for managing a hydrocarbon release comprising:
injecting mineral fines into the hydrocarbon release;
measuring characteristics of a hydrocarbon plume resulting from the hydrocarbon release;
determining whether to adjust the injection of the mineral fines based on the measurements; and adjusting the injection based on the determination;
wherein said determining further comprises measuring a parameter indicative of hydrate generation within the hydrocarbon plume.

2. The method of claim 1, wherein the mineral fines comprise a particle size less than 63 microns.

3. The method of claim 1, comprising identifying a source for mineral fines near the hydrocarbon release and obtaining mineral fines therefrom.

4. The method of claim 1, further comprising identifying the mineral fines with an underwater vehicle.

5. The method of claim 1, further comprising positioning dredging equipment and operating the dredging equipment to obtain the mineral fines.

6. The method of claim 1, further comprising positioning injection equipment near the hydrocarbon release and injecting the mineral fines into the hydrocarbon release via the injection equipment.

7. The method of claim 1, further comprising adjusting one or more of injection equipment and dredging equipment based on the determination.

8. The method of claim 1, wherein determining further comprises determining droplet sizes in the hydrocarbon plume using a droplet size sensor.

9. The method of claim 8, wherein the measuring the characteristics of the hydrocarbon plume comprises positioning a sample cylinder until the sample tube extends at least partially into the hydrocarbon plume, closing the ends of the sample cylinder, retracting the sample cylinder from the hydrocarbon plume, and obtaining an image of the filled sample cylinder.

10. The method of claim 1, wherein determining further comprises comparing the characteristics of the hydrocarbon plume before injection of mineral fines to the current characteristics of the hydrocarbon plume.

11. The method of claim 10, further comprising displaying on a monitor the effectiveness of the injecting based on the comparison, wherein displaying on the monitor comprises changing color of the hydrocarbon plume as presented based on the effectiveness of the injecting.

12. The method of claim 1, wherein determining further comprises comparing images of the hydrocarbon plume before injection of mineral fines to images of the hydrocarbon plume after the injection of the mineral fines.

13. The method of claim 1, wherein measuring the characteristics of the hydrocarbon plume comprises positioning a camera near the hydrocarbon plume and capturing an image of the hydrocarbon plume via the camera.

14. The method of claim 1, wherein the mineral fines comprise particles having a particle size in the range of 3.9 microns to 63 microns as measure along the longest axis.

15. The method of claim 14, wherein at least 80 percent (%) of the mineral fines are within the range of particle size values.

16. A hydrocarbon release management system comprising:
injection equipment configured to inject mineral fines into a hydrocarbon release;
dredging equipment configured to obtain mineral fines from a location near the hydrocarbon release;
a command unit that is a computer system comprising: (i) a processor; (ii) memory in communication with the processor; and (iii) a set of instructions stored on the memory and accessible by the processor, wherein the set of instructions, when executed, are configured to:
receive a transmitted signal from one or more sensors;
determine the characteristics of the hydrocarbon plume based on the transmitted signal; and
based on the determination, provide a visible indication of the effectiveness of the injecting of the mineral fines in creating a dispersion of the hydrocarbon plume;
an underwater vehicle operable to move one or more of the dredging equipment and the injection equipment into a given position, wherein the underwater vehicle is in communication with the command unit and has a propulsion component, a communication component and a measurement module;
wherein the measurement module is configured to measure the characteristics of the hydrocarbon plume and the communication component is configured to communicate signals associated with the measured characteristics of the hydrocarbon plume to the command unit; and
further wherein the measurement module is configured to maneuver a hydrate sensor at least partially into the hydrocarbon plume at a location downstream of the mineral fines injection point, monitor hydrate formation, and transfer hydrate formation data to the command unit.

17. The system of claim 16, wherein the measurement module comprises a camera attached to a retractable line and is configured to:
maneuver the camera to a position adjacent to the hydrocarbon plume and downstream of the injection of the mineral fines;
obtain an image of at least a portion of the hydrocarbon plume; and
transfer the image to the command unit.

18. The system of claim 17, wherein the determination of the characteristics of the hydrocarbon plume is based on the transmitted signal comprises a set of instructions, when executed, configured to:
compare images of the hydrocarbon plume before injection of mineral fines to images of the hydrocarbon plume after injection of the mineral fines; and
display on a monitor the comparison.

19. The system of claim 16, wherein the measurement module is configured to:
maneuver a sampling tube at least partially into the hydrocarbon plume at a location downstream of the mineral fines injection point;
trigger a mechanism to force each end of the sampling tube to close;
maneuver the sampling tube out of the hydrocarbon plume;
obtain an image of the sampling tube; and
transferred the image to the command unit.

20. The system of claim 16, further comprising a set of instructions stored on the memory and accessible by the processor, wherein the set of instructions, when executed, are configured to provide one or more of a visual indication and audible notification associated with effectiveness of the injecting of the mineral fines in creating a dispersion of the hydrocarbon plume.

21. The system of claim 16, wherein the measurement module is configured to:
maneuver a droplet size sensor at least partially into the hydrocarbon plume at a location downstream of the mineral fines injection point;

monitor particle size distribution of hydrocarbon droplets passing through a sampling chamber; and transfer particle size distribution data to the command unit.

22. The system of claim 16, wherein the measurement module is configured to:

maneuver a Sonar system to a portion adjacent to the hydrocarbon plume at a location downstream of the mineral fines injection point;

obtain an image of the hydrocarbon plume based on Sonar backscatter measurements; and transfer the image to the command unit.

\* \* \* \* \*